United States Patent [19]

Murthi et al.

[11] 3,983,121

[45] Sept. 28, 1976

[54] 1-SUBSTITUTED 4-(β-2-QUINOLYLETHYL)PIPERAZINES AND 1,2,3,4-TETRAHYDROQUINOLYL-ETHYL ANALOGUES THEREOF

[75] Inventors: Varanasi Aruna Murthi; Padam Chand Jain; Jitendra Nath Sharma; Rikhab Chand Srimal; Bhola Nath Dhawan; Nitya Anand, all of Lucknow, India

[73] Assignee: Council of Scientific and Industrial Research, New Delhi, India

[22] Filed: July 1, 1974

[21] Appl. No.: 484,527

[52] U.S. Cl. .......................... 260/268 BQ; 424/250
[51] Int. Cl.² .................................. C07D 295/04
[58] Field of Search .............................. 260/268 BQ

[56] References Cited
UNITED STATES PATENTS 3,362,956  1/1968  Archer .................. 260/268 BQ
3,821,228  6/1974  Richards ................ 260/268 BQ

*Primary Examiner*—Paul M. Coughlan, Jr.
*Attorney, Agent, or Firm*—Theodore Post; C. Kenneth Bjork

[57] ABSTRACT

Pharmacologically active 1-substituted 4-(β-2-quinolylethyl)piperazines of the formula

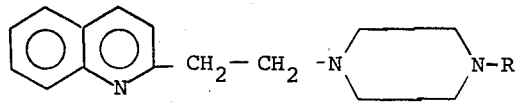

and their 1,2,3,4-tetrahydroquinolylethyl analogues, wherein R represents a lower alkyl, a phenyl, benzyl or a phenethyl group; and pharmaceutically acceptable acid addition and quaternary ammonium salts thereof.

28 Claims, No Drawings

1-SUBSTITUTED 4-β-2-QUINOLYLETHYL)PIPERAZINES AND 1,2,3,4-TETRAHYDROQUINOLYL-ETHYL ANALOGUES THEREOF

SUMMARY OF THE INVENTION

This invention is concerned with novel pharmacologically active substances. More particularly, this invention relates to 1-substituted 4-(β-2-quinolylethyl)-piperazines of the formula

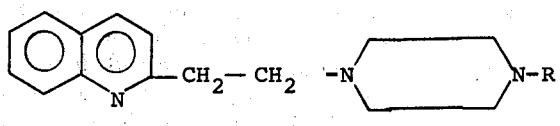

and their 1,2,3,4-tetrahydroquinolylethyl analogues, wherein R represents a lower alkyl, a phenyl, benzyl or a phenethyl group.

In the specification and claims, the terms "lower alkyl" and "lower alkoxy" designate an alkyl or alkoxy group having from 1 to 8 carbon atoms, which may be straight or branched, such as, for example, methyl, ethyl, propyl, isopropyl, butyl, isobutyl, tert-butyl, amyl, isoamyl, etc. and the corresponding alkoxy groups. The term "a phenyl" designates phenyl or a phenyl group substituted by one or more lower alkyl, lower alkoxy, halo or trihaloloweralkyl groups. The term "halo" designates fluoro, chloro or bromo.

A preferred group of compounds includes those in which R is a phenyl group, either unsubstituted or substituted with a lower alkyl group. Preferably, the lower alkyl group is at position 3 of the phenyl radical.

The inventive compounds are prepared by condensing at reflux temperature substantially equimolar amounts of 2-vinylquinoline and an appropriate piperazine, i.e., piperazine having the indicated R substitution, in the presence of a substantially equimolar proportion of a lower aliphatic carboxylic acid as condensing agent and avantageously in the presence of a protic solvent which is preferably a lower alkanol. The 1,2,3,4- positions of the quinoline ring are then hydrogenated to give the corresponding tetrahydro-derivative.

The 1-substituted 4-(β-2-quinolylethyl)-piperazines and their tetrahydrogenated analogues as free bases can, if desired, be converted into their pharmaceutically acceptable acid addition and quaternary ammonium salts. Salts which may thus be formed are, for example, the hydrochloride, hydrobromide, hydroiodide, sulfate, phosphate, acetate, propionate, citrate, tartrate, maleate and malate. Among the useful quaternary ammonium salts are those formed by such lower alkyl halides as methyl iodide and n-hexyl bromide.

The compounds of this invention have useful biological activities, and have in particular high hypotensive activity associated with a low degree of toxicity.

DESCRIPTION OF THE PREFERRED EMBODIMENTS

The general reaction sequence leading to the inventive 1-substituted 4-(β-2-quinolylethyl)piperazines and their 1,2,3,4-tetrahydroquinoline analogues is shown hereinbelow:

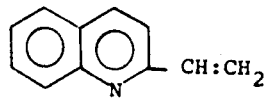

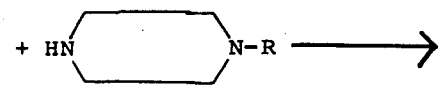

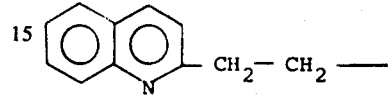

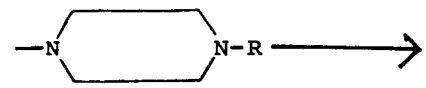

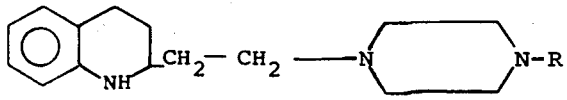

The starting compounds are 2-vinylquinoline and a 1-substituted piperazine. They are reacted in a condensation reaction which is carried out in a protic solvent, advantageously a lower alkanol, e.g., methanol, ethanol, propanol or butanol, by mixing an equimolecular amount of each of the two reactants and of a lower aliphatic monocarboxylic acid, most advantageously acetic acid, the reaction mixture being heated to reflux for a period of about 1 to about 18 hours. The 1-substituted 4-(β-2-quinolylethylpiperazine so obtained is then hydrogenated if the tetrahydro analogue is desired, using hydrogen gas in the presence of a catalyst, preferably a noble metal catalyst such as platinum, palladium or rhodium, with or without a support such as charcoal or alumina. The hydrogenation may also be carried out using nascent hydrogen generated by reaction between an alkali metal such as lithium, sodium or potassium and a lower alkanol such as methanol, ethanol, propanol or butanol, advantageously by adding an excess over the molecular equivalent of the alkali metal to a solution of the 4-(β-2-quinolylethyl)piperazine in the selected alkanol at a temperature up to the boiling point of the solvent. Such alternative reductions will be referred to sometimes as "reducing with hydrogen" or "reduced with hydrogen".

The free base so obtained may be converted into the acid addition or quaternary ammonium salt by simply contacting equimolecular amounts of the base and the selected acid or alkyl halide in a conventional manner.

The following additional description and examples further describe the invention and the manner and process of making and using it to enable the art skilled to make and use the same and set forth the best mode contemplated by the inventors of carrying out the invention.

EXAMPLE 1

1-Phenyl-4-(β-2-quinolylethyl)piperazine

To a mixture of 2-vinylquinoline (0.1 mole, 15g.) and glacial acetic acid (0.1 mole, 6 g.) in ethanol (95%, 100 ml.) N-phenylpiperazine (0.1 mole) was added and the solution was refluxed for 15 hrs. The solvent was removed and the remaining oil was heated in vacuo (1 mm. Hg) to 100°C. The oil left in the flask crystallized out on cooling and was recrystallized from ether-petroleum ether to give the titular product m.p. 79°C.

EXAMPLE 2 to 20

Pursuant to the procedure described in Example 1, the following compounds were prepared:

2. 1-(m-Tolyl)-4-(β-2-quinolylethyl)piperazine by reacting 2-vinylquinoline with N-(m-tolyl)piperazine, m.p. 76° – 7°C.
3. 1-(o-Tolyl)-4-(β-2-quinolylethyl)piperazine by reacting vinylquinoline with N-(o-tolyl)piperazine, m.p. 61°C.
4. 1-(p-Tolyl-4-(β-2-quinolylethyl)piperazine by reacting 2-vinylquinoline with N-(p-tolyl)piperazine, m.p. 88°C.
5. 1-(p-Methoxyphenyl)-4-(β-2-quinolylethyl)-piperazine by reacting 2-vinylquinoline with N-(p-methoxyphenyl)piperazine, m.p. 114°C.
6. 1-(o-Methoxyphenyl-4-(β-2-quinolylethyl)piperazine by reacting 2-vinylquinoline with N-(o-methoxyphenyl)piperazine, m.p. 124°C.
7. 1-(2,5-Xylyl)-4-(β-2-quinolylethyl)piperazine by reacting 2-vinylquinoline with N-(2,5-xylyl)piperazine, m.p. 136°C.
8. 1-(p-Chlorophenyl)-4-(β-2-quinolylethyl)-piperazine by reacting 2-vinylquinoline with N-(p-chlorophenyl)piperazine, m.p. 126°C.
9. 1-(Methyl)-4-(β-2-quinolylethyl)piperazine by reacting 2-vinylquinoline with N-(methyl)piperazine, m.p. 126°C.
10. 1-(o-Chlorophenyl)-4-(β-2-quinolylethyl)piperazine by reacting 2-vinylquinoline with N-(o-chlorophenyl)piperazine, m.p. 84°C.
11. 1-(m-Chlorophenyl)-4-(β-2-quinolylethyl)piperazine by reacting 2-vinylquinoline with N-(m-chlorophenyl)piperazine, m.p. 97°C.
12. 1-(m-Trifluoromethylphenyl)-4-(β-2-quinolylethyl)piperazine by reacting 2-vinylquinoline with N-(m-trifluoromethylphenyl)piperazine, m.p. 94°C.
13. 1-(3,4-Dichlorophenyl)-4-(β-2-quinolylethyl)-piperazine by reacting 2-vinylquinoline with N-(3,4-dichlorophenyl)piperazine, m.p. 88°C.
14. 1-(2,4-Xylyl)-4-(β-2-quinolylethyl)piperazine by reacting 2-vinylquinoline with N-(2,4-xylyl)piperazine, m.p. 126°C.
15. 1-(3,4-Xylyl)-4-(β-2-quinolylethyl)piperazine by reacting 2-vinylquinoline with N-(3,4-xylyl)piperazine, m.p. 108°C.
16. 1-(β-Phenethyl)-4-(β-2-quinolylethyl)piperazine by reacting 2-vinylquinoline with N-(β-phenethyl)piperazine, an oil;
17. 1-(o-Fluorophenyl)-4-(β-2-quinolylethyl)piperazine by reacting 2-vinylquinoline with N-(o-fluorophenyl)piperazine, m.p. 86°C.
18. 1-(m-Fluorophenyl)-4-(β-2-quinolylethyl)piperazine by reacting 2-vinylquinoline with N-(m-fluorophenyl)piperazine, m.p. 84°C.
19. 1-(p-Fluorophenyl)-4-(β-2-quinolylethyl)piperazine by reacting 2-vinylquinoline with N-(p-fluorophenyl)piperazine, m.p. 113°C.
20. 1-Benzyl-4-(β-2-quinolylethyl)piperazine by reacting 2-vinylquinoline with N-benzylpiperazine, an oil.

EXAMPLE 21

1-Phenyl-4-[β-2-(1,2,3,4-tetrahydroquinolyl) ethyl]piperazine

1-Phenyl-4-(β-2-quinolylethyl)piperazine (0.01 mole) was dissolved in dry butanol (100 ml.). Sodium (2 g. atom) was added in small pieces to the solution with occasional stirring. After completion of the addition, the suspension was heated at 120° for 16 hrs. The solvent was removed under vacuum and the residue was taken up in water and extracted with diethyl ether, the extract dried (Na₂SO₄) and evaporated to get the titular tetrahydro compound which was purified by converting it to the hydrochloride which was recrystallized from absolute EtOH-Et₂O mixture, m.p. 198°C.

EXAMPLES 22 to 25

The following tetrahydroquinolylethyl piperazines were prepared pursuant to the procedure of Example 21:

22. 1-(m-Tolyl)-4-[β-2-(1,2,3,4-tetrahydroquinolylethyl)]piperazine hydrochloride.
23. 1-(o-Tolyl)-4-[β-2-(1,2,3,4-tetrahydroquinolylethyl)]piperazine hydrochloride, m.p. 165°C.
24. 1-(p-Tolyl)-4-[β-2-(1,2,3,4-tetrahydroquinolylethyl)]piperazine hydrochloride, m.p. 145°C.
25. 1-(p-Methoxyphenyl)-4-[β-2-(1,2,3,4-tetrahydroquinolylethyl)]piperazine hydrochloride, m.p. 99° – 101°C.

The compounds of the invention all have a marked hypotensive activity. The following pharmacological data, representative of all of the compounds claimed, were obtained by subjecting to animal tests the compound 1-m-tolyl-4-(β-2-quinolylethyl)piperazine.

The LD$_{50}$ in mice was 600 mg./kg. intraperitoneally.

In cats anesthesized with 30 mg./kg. of sodium pentobarbital, the compound produced dose dependant sustained fall of blood pressure starting from a dose of 10 μg./kg. i.v. The hypotension at 10 μg./kg. was 20 mm./Hg for about an hour and at 100 μg./kg. it was 45 mm./Hg for about 1½ hours. At doses of 0.5 mg./kg. and higher, the hypotension was more than 90 mm./Hg for more than 2 hours.

Intraduodenal administration of 1.0 to 2.5 mg./kg. of compound produced hypotension of 40 to 50 mm./Hg for more than 2 hours.

Hypotensive response of the animal remained unaltered after pretreatment with antihistamines and atropine.

In unanesthetised cats, a little higher dose of 0.5 to 2.5 mg./kg. i.v. was required to produce sustained (>1.5 hrs.) hypotension of 40 to 60 mm./Hg in decerebrate spontaneously breathing cats. Similar effect was produced in unanesthetised cats immobilized with d-tubocurarine.

In spontaneously hypertensive rats, the compound was effective in lowering the blood pressure by 50 to 60 mm./Hg for 3 to 4 hrs. in a dose range of 0.5 to 1.0 mg./kg. p.o. The blood pressure was measured by tail plethysmography. Continuous administration of the compound once a day for 15 days did not reveal any potentiation or tolerance to the drug effect.

The compound potentiated adrenaline and noradrenaline responses in blood pressure in cats. Acetylcholine and histamine depressor responses were not significantly affected.

Effect of the compound in vitro was tested in perfused guinea pig heart and in vivo it was studied on cat heart utilizing Cushney's myocardiograph. In low doses (5–10 μg), it had a positive inotropic effect on isolated perfused heart but higher doses depressed it. It, however, potentiated the adrenaline and noradrenaline responses. The compound stimulated both auricles and ventricles in the in vivo preparation up to a dose of 0.1 mg./kg. i.v. Higher doses depressed the heart.

Intravenous administration of the compound (up to 0.1 mg./kg.) produced initial transient respiratory stimulation in cats. Higher doses were followed by marked hypotension and respiratory depression. Doses above 0.5 mg./kg. i.v. produced respiratory failure if the hypotension was too severe.

In mice also the compound caused respiratory depression, but there was no mortality up to a dose of 300.0 mg./kg. i.p.

The compound had a depressant effect on the gross behavior of mice. A dose of 0.5 mg./kg. i.p. antagonized amphetamine-induced hyperactivity by 66% and caused 40% of the mice to fall off in the rota rod test. It, however, had no anti-strychnine effect or anti-metrazol effect up to a dose of 120.0 mg./kg. i.p.

The compound had no significant effect on the isolated guinea pig ileum up to a concentration of $5 \times 10^{-3}$ mg./ml. Higher concentrations had a non-specific spasmolytic effect.

The anti-arrhythmic action of the compound was studied in the isolated guinea pig auricle on the maximum follow through rate. The compound had no significant effect up to a concentration of $3 \times 10^{-3}$ mg./ml.

What is claimed is:

1. A compound which is a member of the group consisting of:
1-(m-tolyl)-4-(β-2-quinolylethyl)piperazine, 1-(m-tolyl)-4-(β-2-quinolylethyl)piperazine hydrochloride, 1-(m-tolyl)-4-[β-2-(1,2,3,4-tetrahydroquinolyl)ethyl]piperazine, 1-(m-tolyl)-4-[β-2-(1,2,3,4-tetrahydroquinolyl)-ethyl]piperazine hydrochloride, 1-(o-tolyl)-4-(β-2-quinolylethyl)piperazine, 1-(p-tolyl)-4-(β-2-quinolylethyl)piperazine, 1-phenyl-4-(β-2-quinolylethyl)piperazine, 1-(p-methoxyphenyl)-4-(β-2-quinolylethyl)piperazine, 1-(o-methoxyphenyl)-4-(β-2-quinolylethyl)piperazine, 1-(2,5-xylyl)-4-(β-2-quinolylethyl)piperazine, 1-(p-chlorophenyl)-4-(β-2-quinolylethyl)piperazine, 1-methyl-4-(β-2-quinolylethyl)piperazine, 1-(o-chlorophenyl)-4-(β-2-quinolylethyl)piperazine, 1-(m-chlorophenyl)-4-(β-2-quinolylethyl)piperazine, 1-(m-trifluoromethylphenyl)-4-(β-2-quinolylethyl)piperazine, 1-(3,4-dichlorophenyl)-4-(β-2-quinolylethyl)piperazine, 1-(2,4-xylyl)-4-(β-2-quinolylethyl)piperazine, 1-(3,4-xylyl)-4-(β-2-quinolylethyl)piperazine, 1-(β-phenethyl)-4-(β-2-quinolylethyl)piperazine, 1-(o-fluorophenyl)-4-(β-2-quinolylethyl)piperazine, 1-(m-fluorophenyl)-4-(β-2-quinolylethyl)piperazine, 1-(p-fluorophenyl)-4-(β-2-quinolylethyl)piperazine, 1-benzyl-4-(β-2-quinolylethyl)piperazine, 1-(m-tolyl)-4-[β-2-(1,2,3,4-tetrahydroquinolylethyl)]piperazine, 1-(o-tolyl)-4-[β-2-(1,2,3,4-tetrahydroquinolylethyl)]piperazine, 1-(p-tolyl)-4-[β-2-(1,2,3,4-tetrahydroquinolylethyl)]piperazine and 1-(p-methoxyphenyl)-4-[β-2-(1,2,3,4-tetrahydroquinolylethyl)]piperazine.

2. The compound of claim 1 wherein the compound is 1-(m-tolyl)-4-(β-2-quinolylethyl)piperazine.

3. The compound of claim 1 wherein the compound is 1-(m-tolyl)-4-(β-2-quinolylethyl)piperazine hydrochloride.

4. The compound of claim 1 wherein the compound is 1-(m-tolyl)-4-[β-2-(1,2,3,4-tetrahydroquinolyl)ethyl]piperazine.

5. The compound of claim 1 wherein the compound is 1-(m-tolyl)-4-[β-2-(1,2,3,4-tetrahydroquinolyl)ethyl]-piperazine hydrochloride.

6. The compound of claim 1 wherein the compound is 1-(o-tolyl)-4-(β-2-quinolylethyl)piperazine.

7. The compound of claim 1 wherein the compound is 1-(p-tolyl-4-(β-2-quinolylethyl)piperazine.

8. The compound of claim 1 wherein the compound is 1-phenyl-4-(β-2-quinolylethyl)piperazine.

9. The compound of claim 1 wherein the compound is 1-(p-methoxyphenyl)-4-(β-2-quinolylethyl)piperazine.

10. The compound of claim 1 wherein the compound is 1-(o-methoxyphenyl)-4-(β-2-quinolylethyl)piperazine.

11. The compound of claim 1 wherein the compound is 1-(2,5-xylyl)-4-(β-2-quinolylethyl)piperazine.

12. The compound of claim 1 wherein the compound is 1-(p-chlorophenyl)-4-(β-2-quinolylethyl)piperazine.

13. The compound of claim 1 wherein the compound is 1-methyl-4-(β-2-quinolylethyl)piperazine.

14. The compound of claim 1 wherein the compound is 1-(o-chlorophenyl)-4-(β-2-quinolylethyl)piperazine.

15. The compound of claim 1 wherein the compound is 1-(m-chlorophenyl)-4-(β-2-quinolylethyl)piperazine.

16. The compound of claim 1 wherein the compound is 1-(m-trifluoromethylphenyl)-4-(β-2-quinolylethyl)-piperazine.

17. The compound of claim 1 wherein the compound is 1-(3,4-dichlorophenyl)-4-(β-2-quinolylethyl)piperazine.

18. The compound of claim 1 wherein the compound is 1-(2,4-xylyl)-4-(β-2-quinolylethyl)piperazine.

19. The compound of claim 1 wherein the compound is 1-(3,4-xylyl)-4-(β-2-quinolylethyl)piperazine.

20. The compound of claim 1 wherein the compound is 1-(β-phenethyl)-4-(β-2-quinolylethyl)piperazine.

21. The compound of claim 1 wherein the compound is 1-(o-fluorophenyl)-4-(β-2-quinolylethyl)piperazine.

22. The compound of claim 1 wherein the compound is 1-(m-fluorophenyl)-4-(β-2-quinolylethyl)piperazine.

23. The compound of claim 1 wherein the compound is 1-(p-fluorophenyl)-4-(β-2-quinolylethyl)piperazine.

24. The compound of claim 1 wherein the compound is 1-benzyl-4-(β-2-quinolylethyl)piperazine.

25. The compound of claim 1 wherein the compound is 1-(m-tolyl)-4-[β-2-(1,2,3,4-tetrahydroquinolylethyl)]piperazine.

26. The compound of claim 1 wherein the compound is 1-(o-tolyl)-4-[β-2-(1,2,3,4-tetrahydroquinolylethyl)-]piperazine.

27. The compound of claim 1 wherein the compound is 1-(p-tolyl)-4-[β-2-(1,2,3,4-tetrahydroquinolylethyl)]-piperazine.

28. The compound of claim 1 wherein the compound is 1-(p-methoxyphenyl)-4-[β-2-(1,2,3,4-tetrahydroquinolylethyl)]piperazine.

* * * * *